(12) United States Patent
Jacobson et al.

(10) Patent No.: US 6,479,708 B1
(45) Date of Patent: Nov. 12, 2002

(54) BIPHASIC CATALYSIS IN WATER/CARBON DIOXIDE MICELLAR SYSTEMS

(75) Inventors: Gunilla B. Jacobson, Los Alamos, NM (US); William Tumas, Los Alamos, NM (US); Keith P. Johnston, Austin, TX (US)

(73) Assignee: The Regents of the University of California, Los Alamos, NM (US)

( * ) Notice: Subject to any disclaimer, the term of this patent is extended or adjusted under 35 U.S.C. 154(b) by 0 days.

(21) Appl. No.: 09/442,873

(22) Filed: Nov. 18, 1999

Related U.S. Application Data (60) Provisional application No. 60/109,079, filed on Nov. 18, 1998.

(51) Int. Cl.$^7$ .......................... C07C 45/00; C07C 29/00; C07C 27/00
(52) U.S. Cl. ....................... 568/451; 568/554; 568/850; 568/907
(58) Field of Search .............................. 568/454, 451, 568/969, 850; 516/209

(56) References Cited

U.S. PATENT DOCUMENTS

| | | | |
|---|---|---|---|
| 31,812 A | 3/1861 | Kuntz | 568/454 |
| 5,198,589 A | 3/1993 | Rathke et al. | 268/454 |
| 5,241,048 A | 8/1993 | Barstow et al. | 530/334 |
| 5,463,082 A | 10/1995 | Horvath et al. | 549/46 |
| 5,559,198 A | 9/1996 | Eian | 526/89 |
| 5,618,894 A | 4/1997 | DeSimone et al. | 526/89 |
| 5,639,910 A | 6/1997 | Ikariya et al. | 562/609 |
| 5,679,737 A | 10/1997 | DeSimone | 524/529 |
| 5,733,964 A | 3/1998 | Johnston et al. | 524/505 |
| 5,739,223 A | 4/1998 | DeSimone | 526/89 |
| 5,789,505 A | 8/1998 | Wilkinson et al. | 526/209 |
| 5,814,678 A | 9/1998 | Randolph | 522/18 |
| 5,824,726 A | 10/1998 | DeSimone et al. | 524/424 |

OTHER PUBLICATIONS

Chen et al, A Novel Water–Soluble Rhodium–Poly(enolate–co–vinyl alcohol–co–vinyl acetate) Catalyst for the Hydroformylation of Olefins, 1997, vol. 199 (5), pp. 893–895.

Johnston et al, Water in–Carbon Dioxide Microemulsions: An Environment for Hydrophiles Including Proteins, Sience, vol. 2712 Feb. 1996.

Joo et al, Molecular catalysis in liquid multiphase systems, AN 1998:325879 Caplus ABS and Citation.

Bhalchandra M. Bhanage et al., "Multiphase Catalysis Using Water–Soluble Metal Complexes in Supercritical Carbon Dioxide," Chem Commun, 1999, pp. 1277–1278.

Brian E. Hanson et al., "Amphiphilic Phosphines for Catalysis in the Aqueous Phase," Catalysis Today, 1998, pp. 421–429.

K.P. Johnston et al., "Water–in–Carbon Dioxide Microemulsions: An Environment for Hydrophiles Including Proteins," Science, vol. 271, Feb. 2, 1996, pp. 624–626.

S.S. Divekar et al., "Selectivity in Hydroformylatoin of 1–decene by Homogeneous Catalysis," Journal of Molecular Catalysis 91, 1994, pp. L1–L6.

Youssef Amrani et al., "Chiral Sulfonated Phosphines: Syntheses and Use as Ligand in Asymmetric Hydrogenation Using an Aqueous–Organic Two–Phase Solvent System," Organometallics, 1989, 8, pp. 542–547.

Sabine Kainz et al., "Perfluoroalkyl–Substituted Arylphosphanes as Ligands for Homogeneous Catalysis in Supercritical Carbon Dioxide," Angew. Chem. Int. Ed. Engl., 1997, 36 No. 15, pp. 1628–1630.

Thomas Burgemeister et al., "[(PP)$_2$RhH] and [(PP)$_2$Rh][O$_2$CH] Complexes as Models for the Catalytically Active Intermediates in the Rh–Catalyzed Hydrogenation of $CO_2$ to HCOOH," Angew. Chem. Int. Ed. Engl., 1993, 32, No. 5, pp. 739–741.

Francois Hutschka et al., "Mechanistic Aspects of the Rhodium–Catalyzed Hydrogentation of $CO_2$ to Formic Acid—A Theorectical and Kinetic Study," J. Am. Chem. Soc., 1997, 119, pp. 4432–4443.

Franz Gassner et al., "$CO_2$ Activation. 7. Formation of the Catalytically Active Intermediate in the Hydrogenation of Carbon Dioxide to Formic Acids Using the [{(COD)Rh($\mu$H)]$_4$/Ph$_2$P(CH$_2$)$_4$PPh$_2$ Catalyst: First Direct Observation of Hydride Migration from Rhodium to Coordinated 1, 5–Cyclooctadiene," Organometallics, 1996, 15, pp. 2078–2082.

Richard M. Lemert et al., "Reverse Micelles in Supercritical Fluids. 3. Amino Acid Solubilization in Ethane and Propane," J. Phys. Chem, 1990, 94, pp. 6021–6028.

Imre Toth et al., "Alternative Supported Aqueous–Phase Catalyst Systems," Journal of Molecular Catalysis A: Chemical, 116, 1997 pp. 217–229.

(List continued on next page.)

*Primary Examiner*—Sreeni Padmanabhan
*Assistant Examiner*—Sikarl A. Witherspoon
(74) *Attorney, Agent, or Firm*—Bruce H. Cottrell (57) ABSTRACT

A process is provided for catalyzing an organic reaction to form a reaction product by placing reactants and a catalyst for the organic reaction, the catalyst of a metal complex and at least one ligand soluble within one of the phases of said aqueous biphasic system, within an aqueous biphasic system including a water phase, a dense phase fluid, and a surfactant adapted for forming an emulsion or microemulsion within the aqueous biphasic system, the reactants soluble within one of the phases of the aqueous biphasic system and convertible in the presence of the catalyst to a product having low solubility in the phase in which the catalyst is soluble; and, maintaining the aqueous biphasic system under pressures, at temperatures, and for a period of time sufficient for the organic reaction to occur and form the reaction product and to maintain sufficient density on the dense phase fluid, the reaction product characterized as having low solubility in the phase in which the catalyst is soluble.

28 Claims, 4 Drawing Sheets

OTHER PUBLICATIONS

Boy Cornils et al., "Introducing TPPTS and Related Ligands for Industrial Biphasic Processes," Journal of Organometallic Chemistry 502, 1995, pp. 177–186.

Tamas Bartik et al., "Surface Active Phosphines for Catalysis Under Two–Phase Reaction Conditions," Journal of Molecular Catalysis A: Chemical 98, 1995, pp. 117–122.

Ferenc Joo et al., Recent Developments in Aqueous Organometallic Chemistry and Catalysis, Journal of Molecular Catalysis A: Chemical 116, 1997, pp. 3–26.

J.W. Rathke et al., "Propylene Hydroformylation in Supercritical Carbon Dioxide," Organometallics, 1991, 10, pp. 1350–1355.

David A. Morgenstern et al., "Supercritical Carbon Dioxide as a Substitute Solvent for Chemical Synthesis and Catalysis," Green Chemistry, 1996, pp. 132–151.

Wolfgang A. Herrmann et al., "Water–Soluble Ligands, Metal Complexes, and Catalysts, Synergism of Homogeneous and Heterogeneous Catalysis," Agnew. Chem. Int.Ed. Engl., 1993, pp. 1524–1544.

Gunilla B. Jacobson et al., "Organic Synthesis in Water/Carbon Dioxide Emulsions," J. Org. Chem. 1999, 64, pp. 1207–1210.

Gunilla B. Jacobsen et al., "Organic Synthesis in Water/Carbon Dioxide Microemulsions," J.Org. Chem, 1999, 64, pp. 1201–1206.

BIPHASIC CATALYSIS IN WATER/CARBON DIOXIDE MICELLAR SYSTEMS

The present application claims the benefit of U.S. provisional application 60/109,079, filed on Nov. 18, 1998.

FIELD OF THE INVENTION

The present invention relates to catalysis in water/dense phase fluid systems, e.g., water/carbon dioxide systems. This invention was made with government support under Contract No. W-7405-ENG-36 awarded by the U.S. Department of Energy. The government has certain rights in the invention.

BACKGROUND OF THE INVENTION

Heterogeneous catalysts currently dominate the field of large-scale industrial chemical synthesis, as the catalyst can easily be separated and reused after the reaction is complete. Homogeneous catalysts typically operate at milder temperatures and can exhibit activities and selectivities unknown by their heterogeneous counterparts, although problems associated with the separation, recovery and re-use of typically highly expensive homogeneous catalysts can sometimes be a limitation. Homogeneous catalysis is, however, widely used in specialty applications, such as production of pharmaceuticals, where high selectivity is of great importance.

Rapid developments in the field of catalysis are leading to an increased demand for tailor-made catalysis. Significant research efforts have been focused upon the immobilization of the organometallic species responsible for catalysis. There have been many reports of "heterogenization" of homogeneous catalysts by tethering them to solid supports such as silica, alumina, polystyrene and water-soluble polymers. The act of supporting these catalysts on a heterogeneous substrate often has a deleterious effect upon their performance and, at best, the performance of such heterogeneous catalysts only approximates those of their homogeneous counterparts. Another disadvantage of supported catalysts is the continuous loss of the metal (leaching) which both contaminates the product phase and increases the production cost due to loss of expensive catalyst.

Other research efforts have been directed to the immobilization of a catalyst in a "mobile phase" such as an aqueous solution immiscible with the product phase. This type of system represents an almost ideal combination of homogeneous and heterogeneous catalysis. Compared to a solid-supported catalyst, it should function more like a homogeneous catalyst and show characteristic features of a homogeneous catalyst, such as higher reactivity, higher selectivity and better reproducibility under mild conditions. This approach has been used in aqueous two-phase catalysis with water-soluble catalyst complexes bearing water-soluble ligands such as sulfonated triarylphosphines (see, for example, U.S. Pat. No. 4,248,802 by Kuntz for catalytic hydroformylation of olefins). The reactants can be either soluble in the water phase or, since the number of water-soluble organic substrates are limited, form a separate phase. The reaction can take place across the interface, in the water phase or in the dense fluid phase depending upon the hydrophilicity of the reactants. The reaction rates are then governed by the solubility of the reactant in the water, and due to decreased solubility, reaction rates are often slower than a single-phase homogeneous reaction. If the product is not water-soluble, it can be easily separated from the water-soluble catalyst complex, allowing the catalyst complex to be recycled.

Current industrial applications of water-soluble catalysts are generally limited to substrates with significant water solubility. The well-known Rhone-Poulenc process for hydroformylation of propene to butanal on a scale of around 330,000 tons per year takes advantage of a water-soluble catalyst. That process cannot be effectively extended to longer chain olefins due to their negligible solubility in water. Mass transport limitations for longer chain olefins across a phase boundary lead to significantly lower reaction rates. The ability to use water-soluble catalysts with hydrophobic or poorly water-soluble substrates remains a major challenge, not only in the hydroformylation of longer chain olefins, but also in catalytic transformations of hydrophobic substrates in general.

A number of investigators have tried to overcome the mass transfer limitations of a two-phase system by addition of either a phase transfer catalyst (PTC) or an interfacially active amphiphilic surfactant. In the case of a PTC (typically a quaternary ammonium compound), a complex is generally formed between the PTC and either (a) the catalyst in the aqueous phase whereafter the catalyst can be transported into the organic phase, or (b) the hydrophobic compound whereafter the hydrophobic compound can be transported into the aqueous phase (see Starks et al., Phase Transfer Catalysis, Chapman and Hall, New York, 1994). A major disadvantage of using a PTC is that it further complicates the purification step as the PTC is slightly soluble in both phases and cannot be easily separated into the aqueous phase for recycle.

The addition of a surfactant in a two-phase system can allow micelles of, e.g., the water phase, to be dispersed in the second phase, typically an organic phase, which significantly increases the surface area between the two phases, reaching values as high as $10^5$ square meter per liter of microemulsion. The surfactant can also lower the surface tension between the two phases, further promoting the reaction across the interface. Although numerous studies of organic reactions have been reported in microemulsions (optically transparent microheterogeneous systems with droplet sizes from about 2 Å to about 500 Å), extremely few have been reported in emulsions (milky-white opaque systems with droplet sizes greater than about 500 Å), with the exception of heterogeneous polymerizations. The difficulty in breaking an emulsion or microemulsion composed of water and an organic solvent is a formidable problem. Another problem with microemulsions is that it is often necessary to add a cosolvent to achieve the proper balance of attractive and repulsive interactions on the hydrophobic and hydrophilic sides of the interface. While the cosolvent can reduce the interfacial tension between the droplets and the continuous phase, it can cause further separation problems.

Other recent approaches have been reported to overcome mass transfer limitations using organic solvents in biphasic catalysis. In one approach, Horvath et al., U.S. Pat. No. 5,463,082, describe catalysts that are soluble in fluorocarbons. Heating these systems in a fluorocarbon and hydrocarbon solvent mixture leads to a miscible homogeneous reaction mixture, which can be separated into two phases, a hydrocarbon/product phase and a fluorocarbon/catalyst phase, upon cooling after reaction.

Recently, micellar solutions of water in supercritical carbon dioxide were reported (see, Johnston et al., Science, vol. 271, pp.264, 1996). Supercritical fluids (i.e., the state of a compound when it is at or above its critical temperature and critical pressure) have liquid-to-gas like densities, higher diffusivities and lower viscosities, all due to the highly compressable nature of the fluid. There are also literature reports of using supercritical fluids, especially supercritical carbon dioxide, as solvents in homogeneous catalysis. In U.S. Pat. No. 5,198,589 by Rathke et al., cobalt carbonyl catalyzed hydroformylation was conducted in a single phase reaction medium of supercritical carbon dioxide. Carbon dioxide is an attractive alternative to organic solvents as it is environmentally benign, essentially nontoxic, inexpensive, nonflammable, has low critical conditions ($P_c$=73.8 bar, $T_c$=31° C.) and can be easily recycled. Supercritical fluids also share many of the advantages of gases including miscibility with other gases, low viscosity, and high diffusivities, thereby providing enhanced heat transfer and the potential for faster reactions, particularly diffusion controlled reactions involving gaseous reactants such as hydrogen, oxygen and carbon monoxide. The density of the fluid, which may be adjusted with temperature and pressure, has a large effect on the solvation of the surfactant tail, and thus the phase behavior and stability of the microemulsion or emulsion. Density effects on water-in-supercritical fluid microemulsions have been explained experimentally and theoretically. The interfacial tension, ($\gamma$), between water and carbon dioxide (18 $mNm^{-1}$ at pressures above 70 bar) is much lower as compared to water and an organic solvent (30–50 $mNm^{-1}$). This eliminates the need of any cosolvents and also further promotes reactions across the interface. Lower $\gamma$ values reflect the fact that carbon dioxide is more miscible with water than typical non-polar organics, largely due to the acidity and quadrupole moment of carbon dioxide. Another important advantage of using carbon dioxide as the dispersed phase is that emulsions are easily broken by rapidly reducing the pressure, separating the water and carbon dioxide into separate phases. The carbon dioxide phase can be subsequently removed simply by vaporization. The micellar system type, i.e., microemulsion or emulsion, is governed by the type and amount of the surfactant, and the volume fractions of the water to carbon dioxide.

A catalytic system or process which overcomes these obstacles of a) separating the product from the catalyst and recycling the latter, b) decreasing mass-transfer limitations by micellar catalysis (i.e., increased surface area and decreased interfacial tension), and c) when using carbon dixoide, removal of all organic solvents for the use of environmentally benign water and carbon dioxide has now been developed using a water/dense phase fluid, e.g., carbon dioxide, micellar reaction system with the catalyst complex and reaction products each soluble in a separate phase.

It is an object of this invention to provide a process for conducting organic reactions in an aqueous biphasic reaction system employing a catalyst for a selected organic reaction, the catalyst either water-soluble or dense phase fluid-soluble and the reaction product soluble in the phase in which the catalyst is insoluble, wherein the reaction products and catalyst can be readily separated by a phase separation.

Another object of this invention is a process for conducting organic reactions in an aqueous biphasic reaction system wherein the reaction rate is enhanced by employment of an aqueous biphasic system including a water phase, a dense phase fluid, a surfactant adapted for forming an emulsion or microemulsion within said aqueous biphasic system, and a catalyst for the selected organic reaction, the catalyst comprised of a metal complex, e.g., a transition metal complex, and at least one ligand, the ligand or ligands soluble in either the water phase or the dense phase fluid.

Another object of this invention is a process for conducting organic reactions in an aqueous biphasic reaction system wherein the reaction rate is enhanced from one or more factors such as gas miscibility, lower surface tension, and increased surface area.

It is another object of this invention to provide an aqueous biphasic reaction mixture including a water phase, a dense phase fluid, and a surfactant adapted for forming an emulsion or microemulsion within said aqueous biphasic system, and a catalyst for a selected organic reaction, the catalyst comprised of a metal complex, e.g., a transition metal complex, and at least one ligand, the ligand or ligands soluble in either the water phase or the dense phase fluid.

Still another object of this invention is to provide a aqueous biphasic reaction mixture including a water phase, a dense phase fluid, and a surfactant adapted for forming an emulsion or microemulsion within said aqueous biphasic system, a catalyst for a selected organic reaction, the catalyst comprised of a metal complex, e.g., a transition metal complex, and at least one ligand, the ligand or ligands soluble in either the water phase or the dense phase fluid, and reactants for said organic reaction, the reactants soluble within one of the phases of the biphasic system.

Yet another object of the present invention is a process of conducting organic reactions such as hydroformylation reactions, hydrogenation reactions including asymmetric or enantioselective hydrogenation reactions, carbon-carbon bond forming reactions, oxidation reactions, and carbonylation reactions within an aqueous biphasic system including a water phase, a dense phase fluid, a surfactant adapted for forming an emulsion or microemulsion within said aqueous biphasic system, and a catalyst for the selected organic reaction, the catalyst comprised of a metal complex, e.g., a transition metal complex, and at least one ligand, the ligand or ligands soluble in either the water phase or the dense phase fluid.

SUMMARY OF THE INVENTION

To achieve the foregoing and other objects, and in accordance with the purposes of the present invention, as embodied and broadly described herein, the process of this invention provides for catalyzing an organic reaction to form a reaction product including placing reactants and a catalyst for the organic reaction, within an aqueous biphasic system including a water phase, a dense phase fluid, and a surfactant adapted for forming an emulsion or microemulsion of said aqueous biphasic system, the catalyst comprised of a metal complex and at least one ligand soluble within one of the phases of the aqueous biphasic system, said reactants soluble within one of the phases of said aqueous biphasic system and convertible in the presence of the catalyst to a product having low solubility within the phase of said aqueous biphasic system in which the catalyst is soluble, and maintaining said aqueous biphasic system under pressures, at temperatures, and for a period of time sufficient for said organic reaction to occur and form said reaction product, said reaction product characterized as having low solubility within the phase of said aqueous biphasic system in which the catalyst is soluble.

The present invention further provides a reaction mixture useful for carrying out an organic reaction, said mixture including an aqueous biphasic system including a water phase, a dense phase fluid,.and a surfactant adapted for forming an emulsion or microemulsion within said aqueous biphasic system; a reactant for said organic reaction, said reactant soluble within one of the phases of the biphasic system, and a catalyst for said organic reaction, said catalyst comprised of a metal complex and at least one ligand soluble within one of the phases of the aqueous biphasic system whereby the catalyst is soluble within one of the phases of the aqueous biphasic system.

DETAILED DESCRIPTION

The present invention is concerned with a process involving the following items: (1) performing reactions, such as hydroformylation, hydrogenation including asymmetric hydrogenation, carbon-carbon bond forming (carbon coupling), carbonylation, and oxidation reactions in an aqueous two-phase system with water-soluble catalysts such as previously used in homogeneous reactions thereby allowing simplified recovery of the product as well as essentially complete recovery of the catalysts; (2) utilizing micellar catalysis, i.e., increasing surface area and lowering surface tension, by addition of a surfactant; and, (3) where desirable, replacing organic solvents with an aqueous biphasic system consisting of water and a dense phase fluid such as carbon dioxide. The present invention is also concerned with a process involving the following items: (1) performing reactions, such as hydroformylation, hydrogenation including asymmetric hydrogenation, carbon-carbon bond forming (carbon coupling), carbonylation, and oxidation reactions in an aqueous two-phase system with dense phase fluid-soluble catalysts and a water-soluble reaction product thereby allowing simplified recovery of the product as well as essentially complete recovery of the catalysts; (2) utilizing micellar catalysis, i.e., increasing surface area and lowering surface tension, by addition of a surfactant thereby increasing reaction rates; and, (3) where desirable, replacing organic solvents with an aqueous biphasic system consisting of water and a dense phase fluid such as carbon dioxide. The present invention is also concerned with reaction mixtures used and produced in the processes of the present invention.

Figure 1:
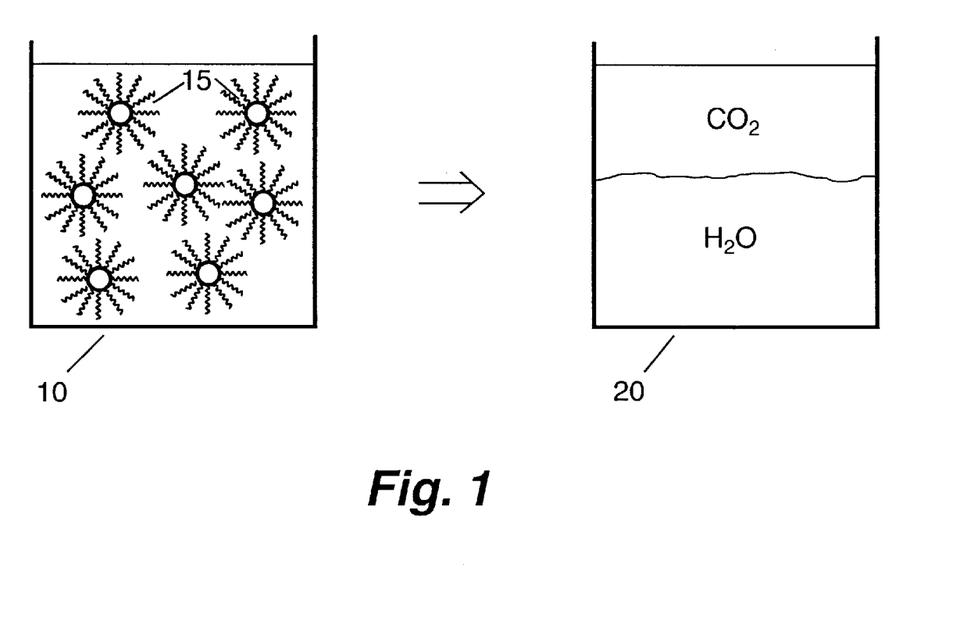
FIG. 1 shows a schematic drawing of a biphasic micellar system wherein the reactions of the present invention are run and the two-phase system resulting from depressurization of the biphasic micellar system used with the present invention.

The biphasic system employed in the present invention can contain water as the continuous phase and a dense phase fluid as the dispersed phase or can contain a dense phase fluid as the continuous phase and water as the dispersed phase. FIG. 1 shows a drawing with one embodiment of a biphasic micellar system 10 wherein the reactions of the present invention are run and the two-phase system 20 resulting from depressurization of the biphasic micellar system used with the present invention. Biphasic micellar system 10 includes micelles 15. In one embodiment, the water phase serves as the catalyst-supporting phase for a water-soluble catalyst. The product or products of such a particular organic reaction are characterized as having low or limited water solubility, i.e., the products or products will be partitioned primarily into the dense phase fluid. In another embodiment, the dense phase fluid serves as the catalyst-supporting phase for a dense phase fluid-soluble catalyst. The product or products of such a particular organic reaction are characterized as having low or limited dense phase fluid solubility, i.e., the products or products will be partitioned primarily into the water phase.

It is desirable that the catalyst ne insoluble or have limited or low solubility in one of the phases of the biphasic micellar system and the product or products of a particular organic reaction to have low or limited solubility in the phase in which the catalyst is soluble. Systems where the product or products have higher solubility, i.e., partition to a greater extent into the phase in which the catalyst is soluble can have value as well as the product or products can simply remain in the phase including the catalyst upon phase separation. However, efficient catalyst recycle makes it especially desirable that the catalyst have as low of solubility as possible in the phase in which the product or products are primarily partitioned. Where the catalyst includes precious metals or expensive ligands this is even more desirable to avoid the loss of catalyst from the system with the product. Generally, where the catalyst contains a non-precious metal, the term "low or limited solubility" can generally refer to amounts of as low as less than about 5 percent by weight, based on total weight of catalyst in the system, while where the catalyst contains a precious metal or expensive ligand, the term "low or limited solubility" would preferably refer to amounts of as low as less than about 1 percent by weight, based on total weight of catalyst in the system.

The dense phase fluid is of a gas (at standard temperature and pressure) that can be compressed to a liquid-like state or a supercritical state and can be,. e.g., a hydrocarbon such as propane, ethane and the like, a halogenated hydrocarbon such as a fluorocarbon, a fluorohydrocarbon, a substituted fluorocarbon, a substituted fluorohydrocarbon and the like, an ether such as dimethyl ether and the like, or carbon dioxide. Preferably, the dense phase fluid is carbon dioxide. No additional solvent is required with such a biphasic system including a dense phase fluid so that the reaction system can be operated free of an organic solvent.

Use of carbon dioxide as the dense phase fluid can have clear advantages, i.e., it is nontoxic, nonflammable, inexpensive, and unregulated. Additional advantages of carbon dioxide include: (1) the surface tension, $\gamma$, between water and carbon dioxide is significantly lower compared to a water/non-polar organic solvent interface; (2) an emulsion with carbon dixoide as the dense phase fluid is easily broken, allowing ready separation of a water-soluble catalyst for subsequent recycle; and, (3) the solubility and diffusivity of potential reactant gases such as hydrogen and carbon monoxide is greater in carbon dioxide than in non-polar organic solvents.

Typically, micelle formation in aqueous solution can be promoted by molecules which contain a long chain (greater than 10 atoms in the chain backbone) hydrophobic alkyl group, and such a long chain hydrophobic alkyl group including heteroatoms other than carbon such as oxygen, sulfur, nitrogen and fluorine or the like, and contain a hydrophilic, ionic head-group (such as tetraalkyl ammonium or sulfonate) at one end. Micelle formation may also be promoted by neutral molecules, which possess a longchain alkyl group as a hydrophobic group in combination with a hydrophilic segment such as a hydroxyl-terminated polyeth- ylene glycol. There are four major classes of surfactants available: anionic, cationic, neutral and amphoteric.

The process of the present invention can be operated at temperatures and pressures such that the dense phase fluid is in the liquid phase or is a supercritical fluid. With the dense phase fluid, the choice of the temperature at which the particular organic reaction is optimally run will determine whether the dense phase fluid is a liquid or is a supercritical fluid. When the desired temperature is above the supercritical temperature of dense phase fluid, the system would likely be comprised of a supercritical phase as the non-aqueous phase.

Several surfactants are known to form microemulsions and emulsions of water and dense phase carbon dioxide. Perfluoropolyether ammonium carboxylate (PFPE) shown below is one example of a anionic surfactant which can be used. Poly(butylene oxide)-b-poly(ethylene oxide) (PBO—b—PEO) shown below is an example of a non-ionic surfactant which can be used. PFPE is commercially available in the COOH form (e.g., from Ausimont under the tradename Fomblin MF300) and can have average molecular weights ranging from about 600 to about 2500 or more. Use of PFPE as the surfactant can allow formation of both water in carbon dioxide or carbon dioxide in water microemulsions, and water in carbon dioxide or carbon dioxide in water emulsions. Use of PBO—b—PEO as the surfactant allows only the formation of emulsions. Other poly(propylene oxide)- and poly(butylene oxide)-based surfactants as described by Johnston et al. in U.S. Pat. No. 5,733,964 may be employed as the surfactants in the present invention. An example of a cationic surfactant considered suitable in the present invention is a fluorochemical cationic surfactant available from Ciba Specialty Chemicals Corporation under the tradename of Lodyne S-106 A shown below.

An example of a PBO—b—PEO type non-ionic surfactant considered suitable in the present invention is available from PPG Industries, Inc. under the tradename SAM-185. Other surfactants capable of forming micelles in a reaction mixture of water and carbon dioxide would be suitable as well and such surfactants will be readily apparent to those skilled in the art.

With the use of various surfactants with PFPE and poly(dimethylsiloxane) (PDMS) tails, the interfacial tension between water and carbon dioxide may be reduced to 1 mNm$^{-1}$ which is sufficiently low to form emulsions or microemulsions. Variations in the chemical structure of the siloxyl monomer of PDMS (i.e. the second component of the copolymer) include ethylene oxide/propylene oxide modified siloxyl monomer, carboxylate modified monomer, and alkane modified monomer.

Surfactant concentrations in the reaction mixtures of the present invention generally range from about 0.1 weight percent, on the basis of the total weight of the reaction mixture, up to about 50 weight percent. Preferably, the surfactant concentrations in the reaction mixtures range from about 0.1 weight percent to about 15 weight percent, and more preferably from about 0.1 weight percent to about 3 weight percent. Higher concentrations of surfactant can be employed where it is desirable to have higher water-to-surfactant values, $W_o$. $W_o$ refers to the mole ratio of water to surfactant.

The weight percent of water to dense phase fluid, preferably carbon dioxide, in the reaction mixtures of the present invention determines whether the reaction mixture forms a microemulsion or an emulsion. The weight percent of water generally ranges from about 0.1 weight percent to about 50 weight percent. Higher weight percentages generally result in the formation of emulsions.

Useful catalysts for the processes of the present invention, such as hydroformylation reactions, hydrogenation reactions, carbonylation reactions, oxidation reactions and carbon-carbon bond forming reactions, can include transition metals. Such transition metals can be selected from the group of cobalt, rhodium, iridium, ruthenium, osmium, molybdenum, tungsten, nickel, palladium and platinum. Other transition metals such as zinc and other metals such as aluminum may also be included in catalysts. Catalysts can be made water-soluble by using water-soluble ligands. Such water-soluble ligands can be chiral ligands or achiral ligands such as generally described by Chao-Jun Li et al. in Organic Reactions in Aqueous Media, John Wiley & Sons, Inc. (1997) and especially. section 5.1 at pages 1 16–123 on Water-Soluble Ligands, such description incorporated herein by reference. Catalysts can be made dense phase fluid-soluble by using dense phase fluid-soluble ligands. Such dense phase fluid-soluble ligands can be, e.g., non-polar fluorinated arylphosphines, non-polar fluorinated alkylphosphines, and siloxane-containing phosphines. Exemplary dense phase fluid-soluble ligands include tris[3,5-bis(trifluoromethyl)phenyl]phosphine and the like or PRR'R$_f$ and PRR'OR$_f$ where R$_f$ is CH$_2$CH$_2$C$_6$F$_{13}$ and R and R' are cyclohexyl or-phenyl. Such dense phase fluid-soluble catalysts can be made by a ligand exchange of such mentioned ligands with, e.g., chloro(1,5-cyclooctadiene) rhodium(I) dimer or chloro(cyclooctene) rhodium(I) dimer in dichloromethane. Other ligands and transition metals may also be used.

One of the most commonly used groups of water-soluble ligands are sulfonated arylphosphines such as mono-sulfonated triphenylphosphines (tppms), di-sulfonated triphenylphosphines (tppds-shown below), or tri-sulfonated triphenylphosphines (tppts). Amphiphilic ligands, i.e., ligands including two types of groups within the ligand, may be employed as well. Also, ligands tethered to surface active agents may be employed as well, such as those described by Hanson et al. in Catalysis Today, vol. 42, pp. 421–429 (1998), such description incorporated herein by reference. Other water soluble ligands (including anionic, cationic, nonionic, and chiral) can also be applied, such as amphos (($C_6H_5$)$_2$PCH$_2$CH$_2$N(CH$_3$)$_3$$^+$I$^-$) and BINAS (sulphonated 2,2'-bis(diphenylphosphinomethyl)-1,1''-binaphthyl -shown below).

Still other water-soluble ligands will be apparent to those of skill in the art.

For hydroformylation reactions and hydrogenation reactions, the well-known water soluble RhCl(tppds)$_3$ catalyst is especially preferred where tppds is a disulphonated triphenylphosphine ligand. This rhodium catalyst complex can be obtained by a simple ligand exchange with the original Wilkinson's catalyst, RhCl(PPh$_3$)$_3$, following the process of equation (1).

Equation (1)

For carbon-carbon bond forming reactions, the known PdCl$_2$(tppds)$_2$ catalyst can be used, obtained by ligand exchange with PdCl$_2$(PhCN)$_2$, following the process of equation (2).

Equation (2)

Chiral water-soluble ligands such as shown below can be synthesized and used for asymmetric hydrogenations, and should give similar results to the standard hydrogenation process. Many other water-soluble catalyst systems may be employed as will be readily apparent to those skilled in the art.

In the catalyst complex, the amount of metal to water-soluble ligand is generally at a ratio of at least 1:1, and as an excess of ligand is preferred may be generally desirable. In the case of hydroformylation reactions, the ratio is preferably from about 1:6 as addition of higher levels of ligand generally will result in a higher straight chain to branched chain (n/i) product ratio.

The catalyst concentration for a process of the present invention is generally from about 0.1 mole percent, on the basis of the total weight of substrate (reactant) and catalyst, to about 15 mole percent. More preferably, the catalyst concentration is from about 1 mole percent to about 10 mole percent for higher production rates of product.

The reactants for the organic reaction are soluble in either the aqueous phase (water) or in the dense phase fluid.

Various classes of catalytic reactions are possible for reaction following the general process presented in the present invention. Such catalytic reactions include hydroformylations, hydrogenations including asymmetric hydrogenations, carbonylations, carbon-carbon bond forming reactions, and oxidation reactions. Other catalytic reactions that may be run in a process in accordance with the present invention will be readily apparent to those skilled in the art.

Hydroformylations (shown by equation (3)), hydrogenations (shown by equation (4)) and carbon-carbon bond forming reactions (shown by equation (5)) of non water-soluble substrates are some of the reactions that can be conducted using the process and reaction mixtures of the present invention.

(3) Hydroforinylation

(4) Hydrogenation where R, R', R'', R''' can be H, CO$_2$R, NO$_2$, CN, COR (5) Carbon-carbon bond forming reactions, e.g.,

((A)—the Heck reaction, Palladium catalyzed arylation and alkylation of olefins);

((B) Suzuki Coupling: Palladium catalyzed arylation and vinylation of boronic acids); and

((C) Stille Coupling: Palladium catalyzed arylation and vinylation with organotrichlorostannanes)

R=aryl, vinyl; X=I, Br, COCl, OTf (triflate), and the like.
(6) Carbonylations a)

X=halide; Nu=nucleophile and, b)

(7) Oxidations (8) Asymmetric hydrogenations

For hydroformylations, the substrates can be olefins, e.g., more specifically, ethylenically unsaturated compounds generally including one or more double bonds, one of which can be a terminal double bond, and having from 2 to 20 or more carbon atoms. The substrate can be a diene or a polyene. The process of the present invention can be especially useful for such substrates containing greater than six carbon atoms. Hydroformylation products of such larger olefins are characterized as having limited solubility in water. Such larger olefins include, e.g., 1-heptene, 1-octene, 1-nonene, 1-decene, 6-propyl-1-decene, 3-undecene, 1-dodecene, 1-tetradecene, 1-pentadecene, 1-hexadecene, 1-heptadecene, 1-octadecene, 1-nonadecene, styrene and the like.

Hydroformylation reactions conducted in accordance with the present invention can utilize partial pressure of carbon monoxide and hydrogen such that the molar ratio of carbon monoxide to hydrogen varies from about 0.1 to about 10. Preferably a molar ratio from about 0.15 to about 0.7 is used. The pressure of the carbon monoxide and hydrogen introduced into the system is generally from about 50 psi to about 350 psi. Additional pressure in the high pressure system is supplied by the dense phase fluid, e.g., by carbon dioxide. The total pressure in the system is generally from about 1000 psi to about 7500 psi.

The substrate concentrations can generally be as high as is permitted in the particular system. The amount of substrate depends upon the overall micellar system with the greatest amount of substrate that is soluble but still able to form micelles. Higher concentrations are generally preferred for greater output. A 1 Molar (M) concentration of the substrate typically would be high with a range of concentration generally being from about 10 milliMolar (mM) up to 1 M or higher.

Reaction conditions in the process of the present invention include a temperature range of from about 10° C. to about 200° C. The temperature must be maintained below the decomposition temperature of any reaction mixture component or any product of the reaction. The temperature for many reactions is often above the critical temperature of supercritical carbon dioxide, i.e., about 31° C. Optimal pressure for the process of the present invention is above the cloud point of the reaction system. The total pressure in the present invention is generally from about 1000 psi to about 7500 psi.

Results are shown for (i) surfactant-free two-phase systems (a system including only water and carbon dioxide), and for (ii) a system including water, carbon dioxide and a surfactant for formation of a microemulsion or emulsion. The data presented below is for some typical non water-soluble substrates but these reactions can be extended to more complex substrates as well.

An example of hydroformylation of a non water-soluble compound is the hydroformylation of 1-decene. The substrate is soluble in supercritical carbon dioxide, as are the two major products, 1-undecanal and 2-methyl decanal. The former product is of interest for perfumery chemicals. The ratio of ligand/Rh is known to effect the ratio of linear to branched aldehyde obtained. A value greater than four increases the amount of linear aldehyde, which is the more desirable product.

Figure 2:
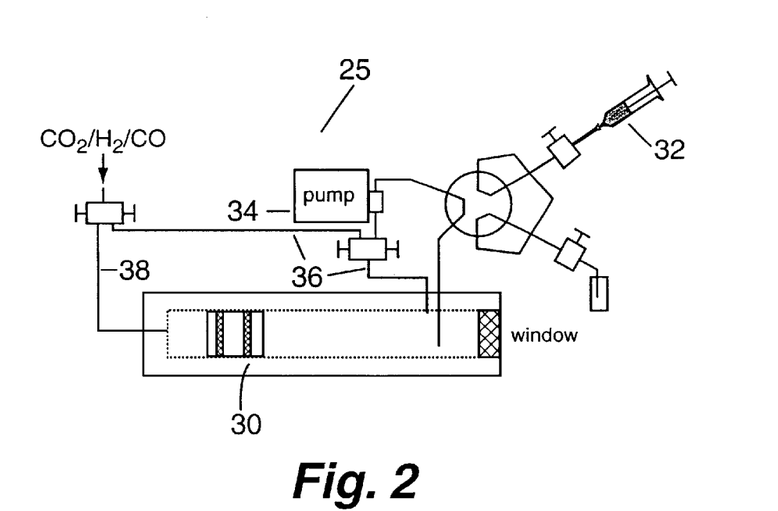
FIG. 2 shows a variable-volume-view cell used in the examples of the present invention.

In the process of the present invention, the reactions can be performed in a variable-volume-cell equipped with a sapphire window for visual inspection of the solvent system. Reactants can be injected into the cell and samples can be taken out of the cell through a 6-port sampling valve. The pressure in the cell can then be adjusted accordingly by an ISCO syringe pump, which is connected directly to the back of the piston in the cell. A pump can be used to recirculate the fluid phase in the cell and together with a stirbar inside the cell enough shear can be obtained to form the micellar phase.

Other reaction cells can be employed as well, including tubes, pipes, autoclaves, and the like. The process can be operated as a continuous flow process or a batch process or by any other suitable process apparent to those of skill in the art.

Under an inert atmosphere such as nitrogen, argon or the like, the reactor can be loaded from the front end with surfactant, water, catalyst and an internal standard. The reactor can then be closed, removed from the inert atmosphere and connected to the pump and gas lines. The reactant gases (hydrogen and carbon monoxide), if used, can be added followed by the desired amount of carbon dioxide. The reactor can be heated in any appropriate fashion, connected to a temperature controller, and pressurized by adding carbon dioxide to the back side of the piston. While heating the cell, the piston can move back accordingly, assuring a constant pressure inside of the cell, and the pump and stir plate can be activated. Once the desired temperature and pressure are achieved inside the cell, the substrate can be injected via the sample loop on the 6-port valve, indicating the start of the particular reaction.

While not wishing to be bound by the present explanation, it is believed that during the reaction the catalyst is located inside the aqueous micelles and the substrate and products are dissolved in the carbon dioxide phase. After depressurizing the system (by releasing the pressure on the piston thereby moving it back to expand the volume and also decreasing the temperature), the micellar system can be broken and a two phase system obtained, consisting of a lower aqueous phase and a carbon dioxide phase, separated by a surfactant layer. The carbon dioxide phase can then be vented from the cell, allowing the products to be collected by tuning the density (i.e., solvent power) of the carbon dioxide phase, as will be readily apparent to those skilled in the art. The vaporized carbon dioxide can be collected and recycled. The surfactant and aqueous catalyst phase are left behind in the reactor, which are reused in the next experiment.

The present invention is more particularly described in the following examples, which are intended as illustrative only, since numerous modifications and variations will be apparent to those skilled in the art.

FIG. 2 shows a variable-volume-view cell 25 used in the examples of the present invention, the cell including piston 30, syringe 32, pump 34, and gas lines 36 and 38.

EXAMPLE 1

Hydroformylation reactions were performed as follows. Under a nitrogen atmosphere, pairs of cells were loaded from the front end with the selected surfactant (0.5 weight percent SAM-185 for the emulsion based on the total weight of water and carbon dioxide, 1.4 weight percent PFPE for the microemulsion based on total weight of water and carbon dioxide, or no surfactant in the case of the two-phase comparison runs performed side-by-side with the surfactant-containing systems), water (4.75 g for the emulsion and comparison run and 75 milligrams (mg) for the microemulsion and comparison run), catalyst (RhCl(tppds)$_3$ or BINAS) and an internal standard of nonane. The cells were sealed, removed from the nitrogen atmosphere and connected to the pump and gas lines. The reactant gases of hydrogen and carbon monoxide were added as a 1:1 ratio mixture at a total pressure of 250 psi followed by the carbon dioxide (4.75 g for the emulsion and comparison run and 9.05 g for the microemulsion and comparison run). The cells were heated to 80° C. by the use of heating tape connected to a temperature controller, and pressurized at 4000 psi by adding carbon dioxide to the back sides of the respective pistons. Once the desired temperature and pressure were achieved inside the cells and the micellar system had formed by stirring and pumping, 1-decene (100 microliters) was injected via the sample loops on the 6-port valve of each cell, initiating the reactions. Samples were taken from the two side-by-side cells after 1.45 hours for the first side-by-side runs including an emulsion system and after 6 hours for the second side-by-side runs including a microemulsion system. The samples were analyzed for percent conversion of the 1-decene, selectivity of conversion to the aldehydes, and the straight to branched ratio of product.

As can be seen in Table 1, the formation of a micellar solution significantly increases the reaction rate and yields; both in the case of emulsion and microemulsion, as compared to a two-phase system. The results are better than previously published data in a two-phase biphasic system and comparable to data obtained by Monflier et al., Angew. Chem. Int. Ed. Engl., vol. 34, pp. 2269–2271 (1995) for addition of, e.g., cyclodextrins, which behave as an inverse phase transfer catalyst. After the reaction was completed decreasing the temperature and pressure broke the micellar solution. $^{31}$P NMR of the remaining aqueous phase showed that most of the catalyst was still intact although some oxidized phosphine ligands were present.

EXAMPLE 2

Hydrogenation reactions were performed as follows: Under a nitrogen atmosphere, two cells were loaded from the front end with the selected surfactant (0.5 weight percent SAM-185 based on total weight of water and carbon dioxide or no surfactant in the case of the two-phase comparison run performed side-by-side with the surfactant-containing system), water (4.75 g), catalyst (RhCl(tppds)$_3$) and an internal standard of nonane. The cells were sealed, removed from the nitrogen atmosphere and connected to the pump and gas lines. The hydrogen was then added (250 psi) followed by the carbon dioxide (4.75 g). The cells were heated to 40° C. by heating tape connected to a temperature controller, and pressurized at 4000 psi by adding carbon dioxide to the back sides of the respective pistons. Once the desired temperature and pressure were achieved inside the cells and the micellar system had formed by stirring and pumping, the reactant, either styrene or 1-decene, was injected via the sample loops on the 6-port valve of each cell, initiating the reactions. Samples were taken from the two side-by-side cells after 1.45 hours for the first side-by-side runs including an emulsion system and at 6 hours for the second side-by-side runs including a microemulsion system. The samples were analyzed for percent hydrogenation of the styrene and the 1-decene.

The results for hydrogenation of styrene (shown by equation (6)) and 1-decene (shown by equation (7)) in a two phase versus emulsion system are shown in Table 2. For both substrates the yields were significantly higher in the emulsion system.

Equation (6)

Equation (7)

In the case of performing asymmetric hydrogenations, the only difference would be the use of a chiral ligand and the same results should be obtained.

TABLE 1

(Hydroformylation of 1-decene[a])

| Biphasic System | wt % H$_2$O | Ligand | wt % H$_2$O | Reaction Time (hours) | mol % catalyst[d] | Conv. (%) | Sel.[e] (%) | ratio n/i[f] |
|---|---|---|---|---|---|---|---|---|
| Two-phase | 50 | tppds | 50 | 1.45 | 2.4 | 63 | 78 | 1.9 |
| Emulsion[b] | 50 | tppds | 50 | 1.45 | 2.4 | 85 | 94 | 1.4 |
| Emulsion[b] | 50 | BINAS | 50 | 4.0 | 2.0 | >99 | 95 | 1.4 |
| Two-phase | 1.1 | tppds | 1.1 | 6.0 hours | 4.0 | 58 | 53 | 2.3 |
| Microemulsion[c] | 1.1 | tppds | 1.1 | 6.0 hours | 4.0 | 80 | 39 | 1.9 |

[a]Reaction conditions: 80° C., 4000 psi.
[b]Using PBO-PEO.
[c]Using PFPE.
[d]Mole percent catalyst to 1-decene.
[e]Selectivity to aldehydes.
[f]Ratio of linear to branched aldehyde.

TABLE 2

(Hydrogenation reaction[a])

| Substrate | wt % H$_2$O | Reaction Time | mol % catalyst[b] | % yield Two-phase | % yield Emulsion[c] |
|---|---|---|---|---|---|
| Styrene | 50 | 6 hours | 6 | 22 | 69 |
| 1-decene | 50 | 3 hours | 1.6 | 10 | 32 |

[a]Reaction conditions: 40° C., 4000 psi.
[b]Mole percent catalyst to substrate.
[c]Using PBO-PEO.

EXAMPLE 3

Hydrogenation reactions in both dense phase (T=28° C.) and supercritical (T=40° C.) carbon dioxide and water emulsions were performed using both nonionic (SAM-185) and cationic (Lodyne S-106A) surfactants. The reactions were performed as in example 2 with the only difference being the amount of surfactant, catalyst and temperature used (see Table 3). Samples were taken after 9 hours from each cell for analysis by gas chromatography (GC). Greater yields of ethyl benzene were obtained using a nonionic surfactant for this particular reaction system, and a higher temperature was also an advantage. In the case of the cationic surfactant the temperature effect was not as noticeable.

TABLE 3

Hydrogenation of Styrene in CO$_2$/H$_2$O Emulsions[a]

| Surfactant | | T (° C.) | CO$_2$-phase | Yield |
|---|---|---|---|---|
| SAM-185 | (nonionic) | 28 | Dense phase | 59% |
| SAM-185 | | 40 | Supercritical | 68% |
| Lodyne 106A | (cationic) | 28 | Dense phase | 23% |
| Lodyne 106A | | 40 | Supercriticial | 20% |

[a]Reaction conditions:, 1 mol % catalyst to substrate, 50 wt % water, 3 wt % surfactant, 4000 psi, 9 h reaction time.

EXAMPLE 4

Figure 3:
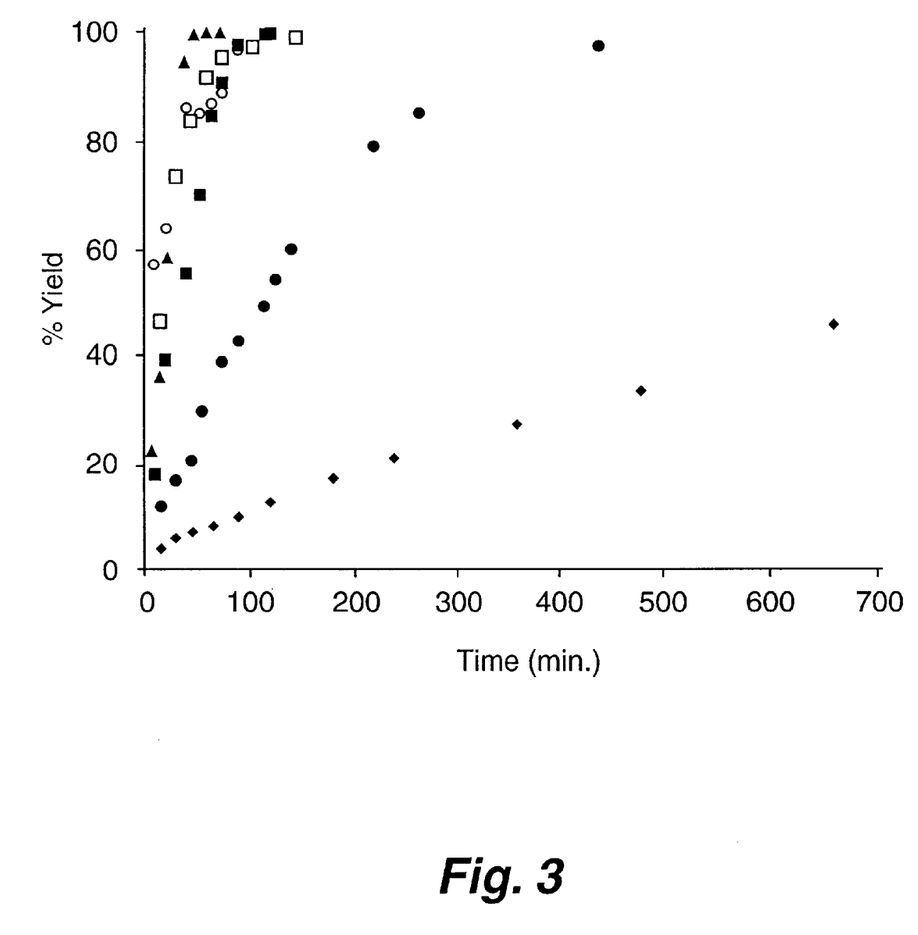
FIG. 3 shows a time profile of formation of ethyl benzene from hydrogenation of styrene performed in biphasic water/carbon dioxide or carbon dioxide/water emulsions using selected surfactants compared with typical reactions performed in biphasic water/toluene or in biphasic water/carbon dioxide.
Figure 4:
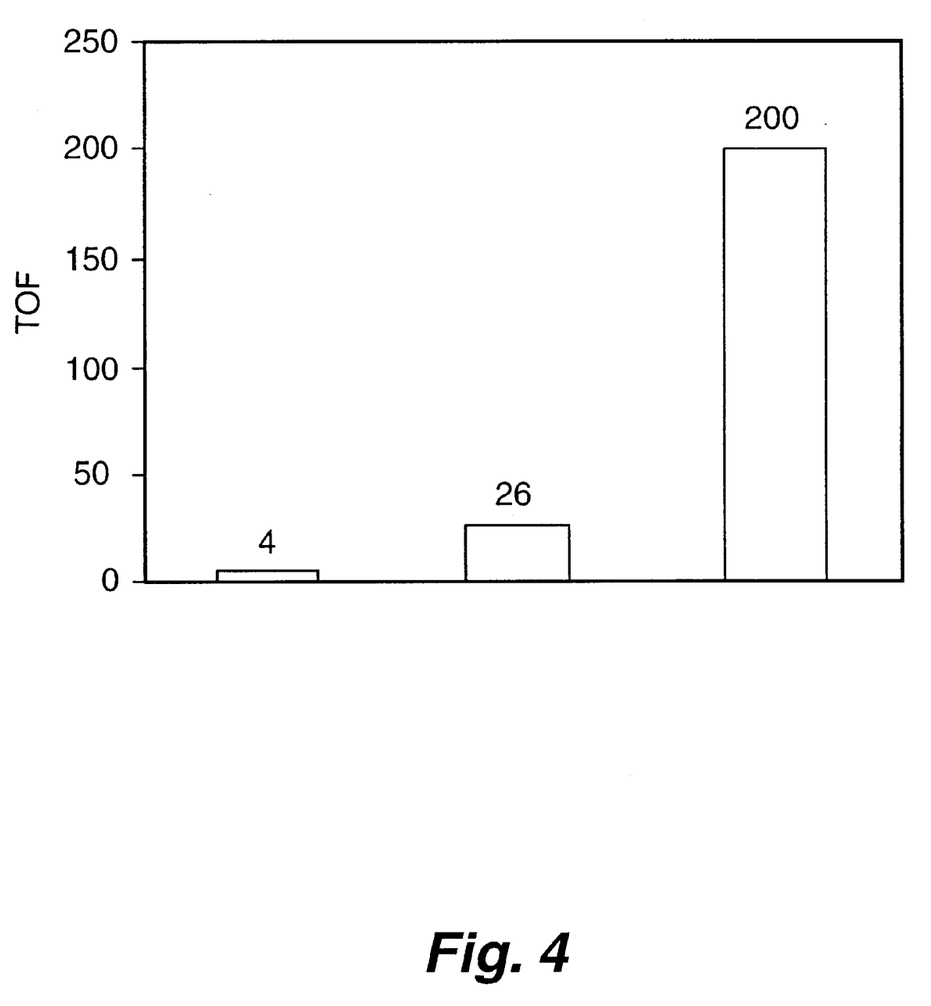
FIG. 4 shows a graph plotting TOF values at 50 percent conversion for a biphasic water/toluene system (A) or in a biphasic water/carbon dioxide system (B) and in biphasic water/carbon dioxide emulsion system (C) as in FIG. 3.

Hydrogenation of styrene: The time profile (formation of product ethyl benzene) for the hydrogenation of styrene is illustrated in FIG. 3 for the three surfactants as well as control experiments run in two-phase water/CO$_2$ and water/toluene systems without added surfactants. Control experiments reveal that the two-phase water/CO$_2$ system is more reactive than the water/toluene system. These results are likely due to higher hydrogen solubility in the CO$_2$ system and potentially also to the lower interfacial tension between water and CO$_2$ as compared to water and traditional organic solvents. While simple solvent replacement of toluene with carbon dioxide leads to some rate enhancement in the present invention, it is clear that this activity is still not practical for most non-polar, nonvolatile substrates. As shown in FIG. 3, the reaction rate for styrene hydrogenation increases significantly upon addition of surfactant and emulsion formation. The time profiles in FIG. 3 suggest the reaction is zero order in substrate throughout the reaction for toluene/water and CO$_2$/water and nearly zero order for at least the first half of the reaction for the emulsions. The initial catalytic activity can be quantified in terms of turnover frequency (TOF), here defined as the mole of substrate transformed per mole of catalyst per hour at 50% conversion. For styrene (FIG. 4) the TOF was found to be 4 h$^{-1}$ in toluene/water, 26 h$^{-1}$ in CO$_2$/water, and 150–300 h$^{-1}$ for the emulsions formed from three different surfactants.

EXAMPLE 5

Pressure effect on the hydrogenation of styrene and 1-decene: Reaction conditions were as in Example 2 except as noted. Using 80 mM of the substrate and 1 mol % of the catalyst RhCl(tppds)$_3$ (Rh/L=⅙) in a 50 weight percent water to CO$_2$, emulsion with 2 weight percent of the PBO—PEO surfactant. T=40° C. and P=4000 psi.

TABLE 4

(Pressure Effect on Hydrogenation reaction[a])

| Substrate | wt % H$_2$O | Reaction Time | mol % catalyst[b] | psi hydrogen | % yield Emulsion[c] |
|---|---|---|---|---|---|
| Styrene | 50 | 20 minutes | 1 | 300 | 45 |
| " | 50 | 40 minutes | 1 | 300 | 65 |
| " | 50 | 60 minutes | 1 | 300 | 80 |
| " | 50 | 100 minutes | 1 | 300 | 85 |
| " | 50 | 20 minutes | 1 | 600 | 65 |
| " | 50 | 40 minutes | 1 | 600 | 95 |
| " | 50 | 60 minutes | 1 | 600 | 98 |
| " | 50 | 100 minutes | 1 | 600 | 98 |
| 1-Decene | 50 | 200 minutes | 1 | 300 | 60 |
| " | 50 | 400 minutes | 1 | 300 | 75 |
| " | 50 | 200 minutes | 1 | 600 | 95 |
| " | 50 | 400 minutes | 1 | 600 | 98 |

[a]Reaction conditions: 40° C., 4000 psi on cell.
[b]Mole percent catalyst to substrate.
[c]Using PBO-PEO.

EXAMPLE 6

Figure 5:
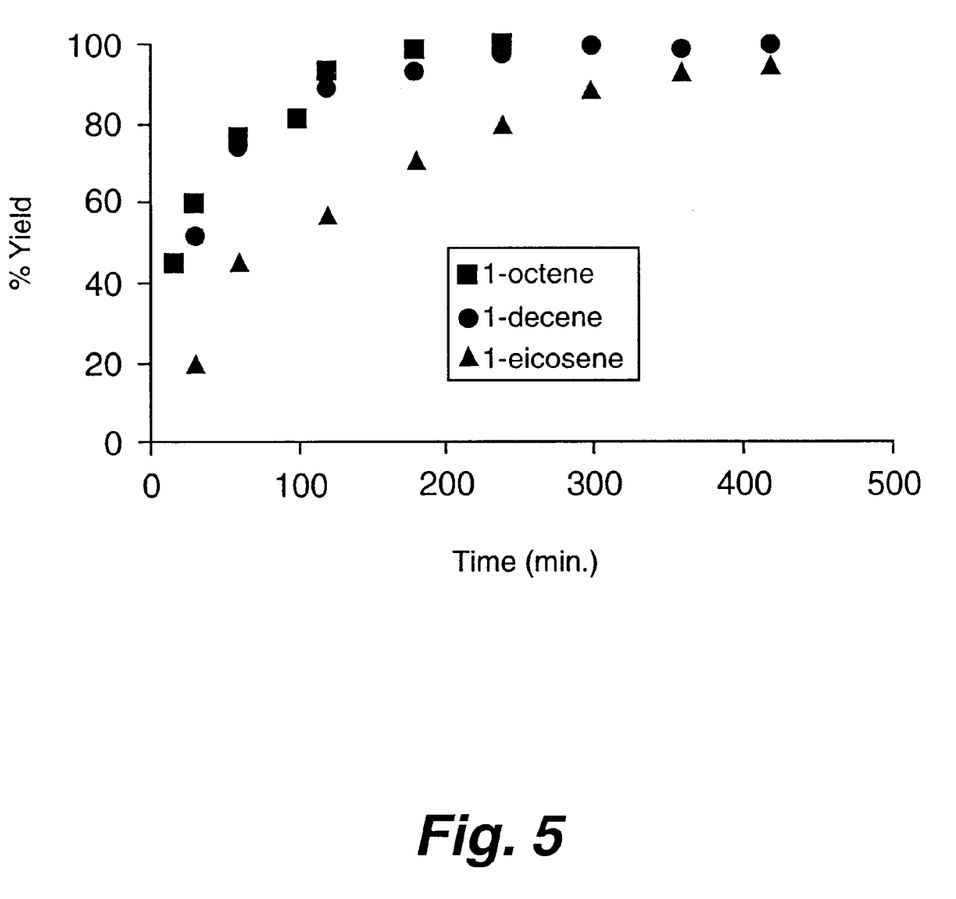
FIG. 5 shows a graph of the yield as a function of time for the hydrogenation of 1-octene, 1-decene and 1-eicosene.

Hydrogenation of long chained olefins: In an effort to ascertain whether the reaction was occurring in the water phase or at the interface, a series of hydrophobic 1-alkenes was examined. The TOF at 50 % conversion for 1-octene, 1-decene and 1-eicosene was measured to be 140 h$^{-1}$, 110 h$^{-1}$ and 30 h$^{-1}$, respectively. If the initial zero order kinetic dependence on substrate concentration arises from a steady state concentration of substrate in the aqueous phase (i.e., the water solubility of the substrate), the relative rates would be expected to correlate with the relative solubility in water for these olefins, since the homogeneous reaction rate is known to be independent of chain length. The solubility of 1-octene in water at 25° C. is 2.7 mg/L water, and the solubility of higher olefins decreases exponentially with molar volume. The observation that 1-eicosene is only about four times slower than 1-octene, despite its markedly lower (orders of magnitude) water solubility indicates that the reaction could be occurring at the interface where the relative concentrations may be much closer, rather than in bulk water.

The reaction conditions were as follows. Using 80 mM of the substrate and 1 mol % of the catalyst RhCl(tppds)$_3$ (Rh/L=⅙) in a 50 weight percent water to CO$_2$ emulsions with 2 weight percent of the PBO—PEO surfactant. T=40° C. and P=4000 psi.

EXAMPLE 7

Recycle data for the hydrogenation of styrene: After performing a hydrogenation reaction of styrene as in example 5 the emulsion was broken by decreasing the pressure to 1200 psi and stopping the stirring and pump. Catalyst recycle was demonstrated by transferring the product containing CO$_2$ phase under pressure to a separate high pressure reactor and then charging the aqueous phase, still containing the catalyst and surfactant, with more H$_2$, CO$_2$ and alkene. Repressurization and recirculation led to emulsion formation. For styrene, it was found that the catalyst activity remains essentially constant for at least three cycles, i.e. complete conversion after 3 h for cycle 1, 2 and 3 respectively, demonstrating efficient catalyst recycle.

EXAMPLE 8

Oxidation of 2-octanol was performed as follows. Pairs of cells were loaded from the front end with 5 mL water, 5 mL 30% $H_2O_2$, 14 mg $Na_2WO_4$, 14 mg methyl 3-tri-n-octylammonium sulfate, and 150 µl decane (used as internal standard). To one of the cells 194 mg SAM-185 was also added. Both cells were closed, connected to the pump, and 9.9 mL $CO_2$ was added. The cells were heated to 90° C. by heating tape connected to a temperature controller, and pressurized to 4000 psi by adding carbon dioxide to the back sides of the respective pistons. Once the desired temperature and pressure was achieved inside the cell and an emulsions had formed in the one containing the surfactant, 344 µl 2-octanol was injected into each cell through the 6-port valve. Samples taken from both cells after 4 hours were analyzed by GC and showed total conversion to 2-octanone for both reaction systems. The oxidation reaction is shown below.

EXAMPLE 9

An example of hydrogenation in a biphasic reverse emulsion with a carbon dioxide-soluble ligand was as follows. A carbon dioxide-soluble catalyst complex was made by a ligand exchange of tris[3,5-bis(trifluoromethyl)phenyl]phosphine with chloro(1,5-cyclooctadiene) rhodium(I) dimer. Water soluble substrates used as examples for hydrogenations in biphasic reverse emulsions included methyl-2-acetamidoacrylate and 2-acetamido acrylic acid. Both were hydrogenated using of the carbon dioixde-soluble RhCl[tris (3,5-bis(trifluoromethyl)phenyl)phosphine]$_2$. Reaction conditions were 80 mM substrate, 1 mol % catalyst, 50 weight percent $H_2O$ to $CO_2$, 2.0 weight percent PBO—PEO surfactant to the total amount of $H_2O$ and $CO_2$, 40° C., 4000 psi.

Methyl-2-acetamidoacrylate was hydrogenated to complete conversion in 1 hour and 2-acetamido acrylic acid to 75 percent yield in 12 hours.

The present results of the examples demonstrate the benefits of the present invention wherein catalyst utilization and recovery brings the advantages of both heterogeneous and homogeneous catalysis. Reactions occur in a homogeneous fluid with enhanced diffusion, gas miscibility, and ability to control selectivity and activity through ligand environment, solvent properties and choice of surfactant. Valuable catalysts can be recovered and reused, opening up a wide range of expensive catalysts for practical commercial use, especially for the synthesis of specialty chemicals. The process of the present invention should help overcome major economic and environmental challenges to catalysis science and industrial practice. It should also produce significant economic and environmental benefit by reducing the use of hazardous solvents, improving the recovery of expensive and possibly toxic catalysts, minimizing waste generation and increasing energy utilization through efficient separation of products, and decreasing capital investments through the reduction in the number of unit operations needed for product synthesis and purification.

Although the present invention has been described with reference to specific details, it is not intended that such details should be regarded as limitations upon the scope of the invention, except as and to the extent that they are included in the accompanying claims.

What is claimed is:

1. A process for catalyzing an organic reaction to form a reaction product comprising:

placing reactants and a catalyst for the organic reaction within an aqueous biphasic system including a water phase, a dense phase fluid of a material that is a gas at standard temperature and pressure, and can be compressed to a liquid-like state or supercritical state, and a surfactant adapted for forming an emulsion or microemulsion of said aqueous biphasic system, the catalyst comprised of a metal complex and at least one ligand soluble within one of the phases of said aqueous biphasic system whereby the catalyst is soluble within one of the phases of said aqueous biphasic system, said reactants soluble within one of the phases of said aqueous aphasic system and convertible in the presence of the catalyst to a product having low solubility within the phase of said aqueous biphasic system in which the catalyst is soluble; and, maintaining said aqueous biphasic system under pressures, at temperatures, and for a period of time sufficient for said organic reaction to occur and form said reaction product and to maintain sufficient density on said dense phase fluid so as to keep said dense phase fluid in a liquid-like state or supercritical state, said reaction product characterized as having low solubility within the phase of said aqueous biphasic system in which the catalyst is soluble.

2. The process of claim 1 wherein said dense phase fluid is liquid carbon dioxide or supercritical carbon dioxide.

3. The process of claim 1 wherein said dense phase fluid is selected from the group consisting of a hydrocarbon, a fluorocarbon, a fluorohydrocarbon, a substituted fluorocarbon, a substituted fluorohydrocarbon, an ether, and carbon dioxide.

4. The process of claim 2 wherein said aqueous/carbon dioxide biphasic system is organic-solvent free.

5. The process of claim 1 wherein the metal complex includes a transition metal selected from the group consisting of cobalt, rhodium, iridium, ruthenium, osmium, molybdenum, tungsten, nickel, palladium and platinum.

6. The process of claim 5 wherein the transition metal is selected from the group consisting of cobalt, rhodium, iridium, ruthenium, osmium, molybdenum, tungsten, nickel, palladium and platinum.

7. The process of claim 1 wherein said catalyst is water-soluble and includes ligands selected from the group of sulphonated arylphosphines, ionic phosphines, cationic phosphines, and polar neutral phosphines, amines, and oxygen-containing ligands.

8. The process of claim 7 wherein said catalyst includes chiral ligands.

9. The process of claim 1 wherein said catalyst is dense phase fluid-soluble and includes ligands characterized as providing solubility in the dense phase fluid.

10. The process of claim 2 wherein said catalyst is carbon dioxide-soluble and includes lipophilic ligands selected from the group of non-polar fluorinated arylphosphines, non-polar fluorinated alkylphosphines, and siloxane-containing phosphines.

11. A reaction mixture useful for carrying out a catalyzed organic reaction, said mixture comprising:

an aqueous biphasic system including a water phase, a dense phase fluid, and a surfactant adapted for forming an emulsion or microemulsion within said aqueous biphasic system;

a reactant for said organic reaction, said reactant soluble within one of the phases of the biphasic system; and a catalyst for said organic reaction, said catalyst comprised of a metal complex with at least one ligand soluble within one of the phases of said aqueous biphasic system whereby the catalyst is soluble within one of the phases of said aqueous biphasic system.

12. The reaction mixture of claim 11 wherein said dense phase fluid is liquid carbon dioxide or supercritical carbon dioxide.

13. The reaction mixture of claim 11 wherein said dense phase fluid is selected from the group consisting of a hydrocarbon, a fluorocarbon, a fluorohydrocarbon, a substituted fluorocarbon, a substituted fluorohydrocarbon, an ether, and carbon dioxide.

14. The reaction mixture of claim 11 wherein said metal complex includes a transition metal. selected from the group consisting of cobalt, rhodium, iridium, ruthenium, osmium, molybdenum, tungsten, nickel, palladium and platinum.

15. The reaction mixture of claim 14 wherein said transition metal is selected from the group consisting of cobalt, rhodium, iridium, ruthenium, .osmium, molybdenum, tungsten, nickel, palladium and platinum.

16. The reaction mixture of claim 11 wherein said catalyst is water-soluble and includes ligands selected from the group of sulphonated arylphosphines, ionic phosphines, cationic phosphines, and polar neutral phosphines, amines, and oxygen-containing ligands.

17. The reaction mixture of claim 16 wherein said catalyst includes chiral ligands.

18. The reaction mixture of claim 11 wherein said catalyst is dense phase fluid-soluble and includes ligands characterized as providing solubility in the dense phase fluid.

19. The reaction mixture of claim 11 wherein said catalyst is carbon dioxide-soluble and includes lipophilic ligands selected from the group of non-polar fluorinated arylphosphines, non-polar fluorinated alkylphosphines, and siloxane-containing phosphines.

20. The reaction mixture of claim 11 wherein said organic reaction is hydroformylation, said reactant is an olefin, diene or polyene and said reaction mixture further includes hydrogen and carbon monoxide to produce an aldehyde or a derivative thereof.

21. The reaction mixture of claim 20 wherein said olefin is selected from the group consisting of olefins, dienes and polyenes.

22. The reaction mixture of claim 16 wherein said catalyst is a transition metal based catalyst.

23. The reaction mixture of claim 11 wherein said organic reaction is hydrogenation, said reactant is a substrate capable of undergoing hydrogenation and said reaction mixture further includes hydrogen.

24. The reaction mixture of claim 23 wherein said catalyst is water-soluble.

25. The reaction mixture of claim 23 wherein said dense phase fluid is carbon dioxide and said catalyst is carbon dioxide-soluble.

26. The reaction mixture of claim 23 wherein at least one water-soluble ligand with said metal complex is a chiral water-soluble catalyst containing an enantiomerically enriched chiral ligand for conducting an enantio selective hydrogenation.

27. The reaction mixture of claim 11 wherein said organic reaction is a carbon-carbon bond forming reaction and said reactant includes a pair of substrates capable of undergoing a carbon-carbon bond forming reaction in the presence of said catalyst.

28. The reaction mixture of claim 11 wherein said organic reaction is oxidation, said reactant is a substrate capable of undergoing oxidation in the presence of said catalyst, and said reaction mixture further includes an oxidant species.

* * * * *